(12) United States Patent
Cantrell et al.

(10) Patent No.: US 6,197,130 B1
(45) Date of Patent: Mar. 6, 2001

(54) METHOD AND APPARATUS TO ACCESS OPTIMUM STRENGTH DURING PROCESSING OF PRECIPITATION STRENGTHENED ALLOYS

(75) Inventors: John H. Cantrell, Yorktown; William T. Yost, Newport News, both of VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/065,986

(22) Filed: Apr. 24, 1998

Related U.S. Application Data
(60) Provisional application No. 60/050,915, filed on Apr. 24, 1997.

(51) Int. Cl.⁷ ........................................... C21D 1/54
(52) U.S. Cl. ............................................ 148/508
(58) Field of Search ................................ 148/508, 510, 148/524

(56) References Cited

U.S. PATENT DOCUMENTS 3,675,472 * 7/1972 Kay et al. .............................. 73/67.5

FOREIGN PATENT DOCUMENTS

414321 * 2/1974 (RU) .................................... 148/508
0648619 * 2/1979 (RU) .................................... 148/508

* cited by examiner

Primary Examiner—Scott Kastler
(74) Attorney, Agent, or Firm—Helen M. Galus

(57) ABSTRACT

A method and apparatus are provided which enable the nondestructive testing of strength of a heat treated alloy. An alloy is insonified with an ultrasonic signal. The resulting convoluted signal is detected and the acoustic nonlinearity parameter is determined. The acoustic nonlinearity parameter shows a peak corresponding to a peak in material strength.

44 Claims, 3 Drawing Sheets

METHOD AND APPARATUS TO ACCESS OPTIMUM STRENGTH DURING PROCESSING OF PRECIPITATION STRENGTHENED ALLOYS

CROSS-REFERENCE

Pursuant to 35 U.S.C. §119, the benefit of priority from provisional application No. 60/050,915, with a filing date of Apr. 24, 1997, is claimed for this non-provisional application.

ORIGIN OF THE INVENTION

The invention described herein was made by an employee of the United States Government and may be manufactured and used by or for the Government for governmental purposes without the payment of any royalties thereon or therefor.

BACKGROUND OF THE INVENTION

1. Technical Field of the Invention

The present invention relates generally to nondestructive measurement of strength of heat-treated precipitation-strengthened alloys and specifically to the monitoring of the harmonic content of an acoustic signal passed through the specimen during the heat treatment process.

2. Discussion of the Related Art

Generally, heat-treatment is performed according to compiled data. A recipe is followed, according to previous experience, to arrive at a heat treatment time which will produce a maximum strength for a given alloy. The compiled data method assumes, however, that the material being treated is identical to those used to compile the data. This is not usually the case as the material is generally not homogeneous in constituent composition and the composition from batch to batch is generally different. Thus such methods can only provide an estimate as to appropriate heat treatment parameters.

Methods of determining strength are known which are destructive, such as tensile or torsional strength tests. Other methods are not as destructive, but only assess surface strength of the material such as surface hardness tests. These methods are static and generally require that the material be removed from the heat treatment process.

A large class of alloys are strengthened by precipitates which contain a different local chemical composition from that of the bulk metal matrix. It has been well established that optimal strength levels may be achieved in certain alloy systems when relatively large strains become set up at or near the interfaces between the precipitates and the surrounding matrix. The strain fields are very effective in blocking the motion of point and line defects through the metal when a load is applied. From a processing standpoint, the maximum strength is achieved by heat treating alloys at the proper temperature for an optimal length of time. During initial hardening, precipitates begin to cluster together in very small groups known as zones. With increased time, the zones grow larger and are known as particles or precipitates and the strain fields become stronger up to a maximum. Aging for too long leads to a decrease in material strength as the strain fields diminish in strength due to continuing growth of the precipitates.

SUMMARY OF THE INVENTION

It is an object of the present invention to provide a method for monitoring a heat treatment process in a nondestructive manner.

It is a further object of the present invention to provide a method which allows for monitoring of the heat treatment process without first stopping the process.

To achieve the forgoing objects a heat treatable alloy is provided. While undergoing heat treatment, also known as artificial aging or precipitation hardening, the material is insonified with ultrasonic waves. The resulting signal is monitored and the acoustic nonlinearity parameter is calculated. The acoustic nonlinearity parameter is then used to predict the strength of the material being interrogated.

The method may of course be used on a specimen that has already undergone heat treatment with similar results. The greatest advantage, however, is realized in real time monitoring of the heat treatment process.

DESCRIPTION OF PREFERRED EMBODIMENTS

A workpiece, made from a heat treatable metallic alloy, is prepared for heat treatment. A transducer is acoustically coupled to the workpiece. The transducer is preferably capable of producing an acoustic signal having a wavelength much larger than the grain and precipitate size of the material to be monitored. The transducer also preferably is capable of producing a signal which is substantially sinusoidal. The transducer is also preferably selected to be able to withstand high temperatures such as those used in heat treatment processes.

As the workpiece is heat treated, it is insonified by the transducer. The resulting signal is monitored. The monitored signal may be treated in a variety of ways. The amplitude of the fundamental signal may be monitored and via a feedback system kept at a constant amplitude. Then, the second harmonic of the signal may be monitored and used to indicate the changes in material strength.

Another method makes use of the same two measurements to calculate a value for the acoustic nonlinearity parameter (see Eq. 1, below for the calculation of the acoustic nonlinearity parameter). Since the acoustic nonlinearity parameter is proportional to the amplitude of the second harmonic signal when the fundamental signal is constant, either value may be conveniently used to monitor changes in material strength. It is important to note, however that if the second harmonic signal is used alone that it must be normalized as described above, by keeping constant the fundamental signal.

For the sake of clarity, only the acoustic nonlinearity parameter will be discussed in the following explanation, however it is evident that the second harmonic signal amplitude could be used in its place. As the heat treatment progresses, the acoustic nonlinearity parameter will display a series of peaks. Each peak corresponds to the dominance of a particular precipitate in its contribution to material strength. In some cases more than one precipitate will form at about the same time so a single peak could correspond to more than one precipitate. In a given alloy, there are a known number of precipitates which contribute to the material's heat treated strength. Thus, for a given alloy there are a given number of peaks expected. Once the peak which corresponds to maximum material strength is determined, the heat treatment process can be controlled through a feedback system, the heat treatment ending when the appropriate peak in acoustic nonlinearity parameter is reached.

EXAMPLE 1

Figure 2:
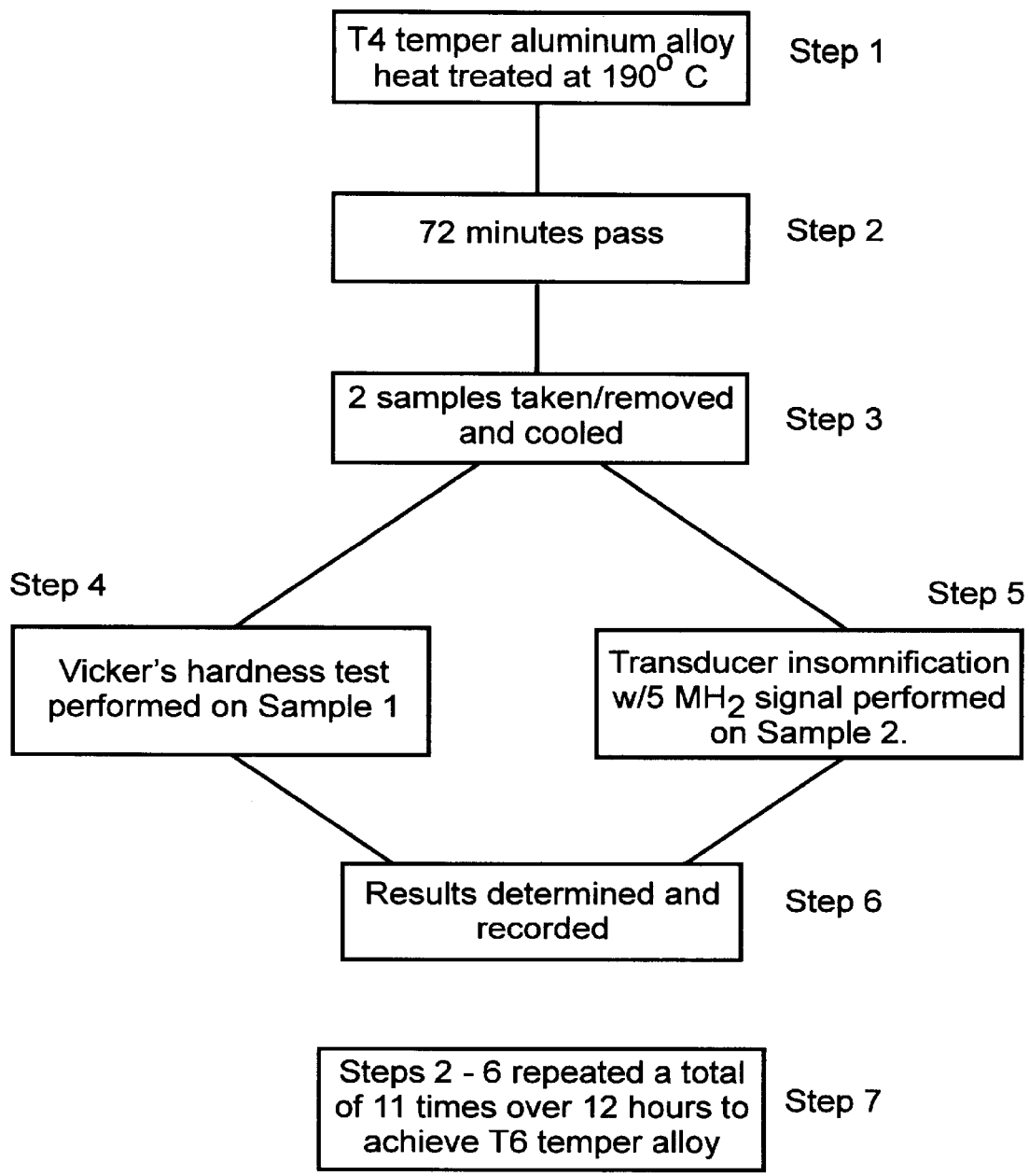
FIG. 2 is a flow chart illustrating steps in one example of the application of the present invention.

In one example of the application of the present invention, the artificial aging of aluminum alloy 2024 from the T4 to the T6 temper was monitored (see FIG. 2). Samples of stock aluminum alloy were heat treated in 72 minute increments at a temperature of 190° C. (step 1) for 12 hours according to ASM standards to obtain the transformation from T4 to the T6 temper (step 7). In order to monitor the changes in the nonlinearity parameter and the hardness during the transformation eleven sets of samples were sectioned in sequence from bar stock, each set consisting of a pair of disks. One set was removed from heat treatment every 72 minutes for the 12 hour duration of the heating and quenched in cold running tap water (steps 2 and 3).

A Vickers hardness test was performed on one of each pair (step 4), the other was insonified by a transducer axially aligned with the sample and producing a 5 MHz ultrasonic signal (step 5). Acoustic harmonic generation measurements were made on each sample and the acoustic nonlinearity parameters were calculated from these measurements in accordance with Eq. 1.

$$\beta = 8/k^2 d\, B_2/A_1^2 \qquad \text{Eq. 1}$$

Where $\beta$ is the acoustic nonlinearity parameter, $A_1$ is the amplitude of the acoustic wave fundamental signal, $B_2$ is the amplitude of the second harmonic signal, d is the wave propagation distance, and k is the wave number.

Figure 1:
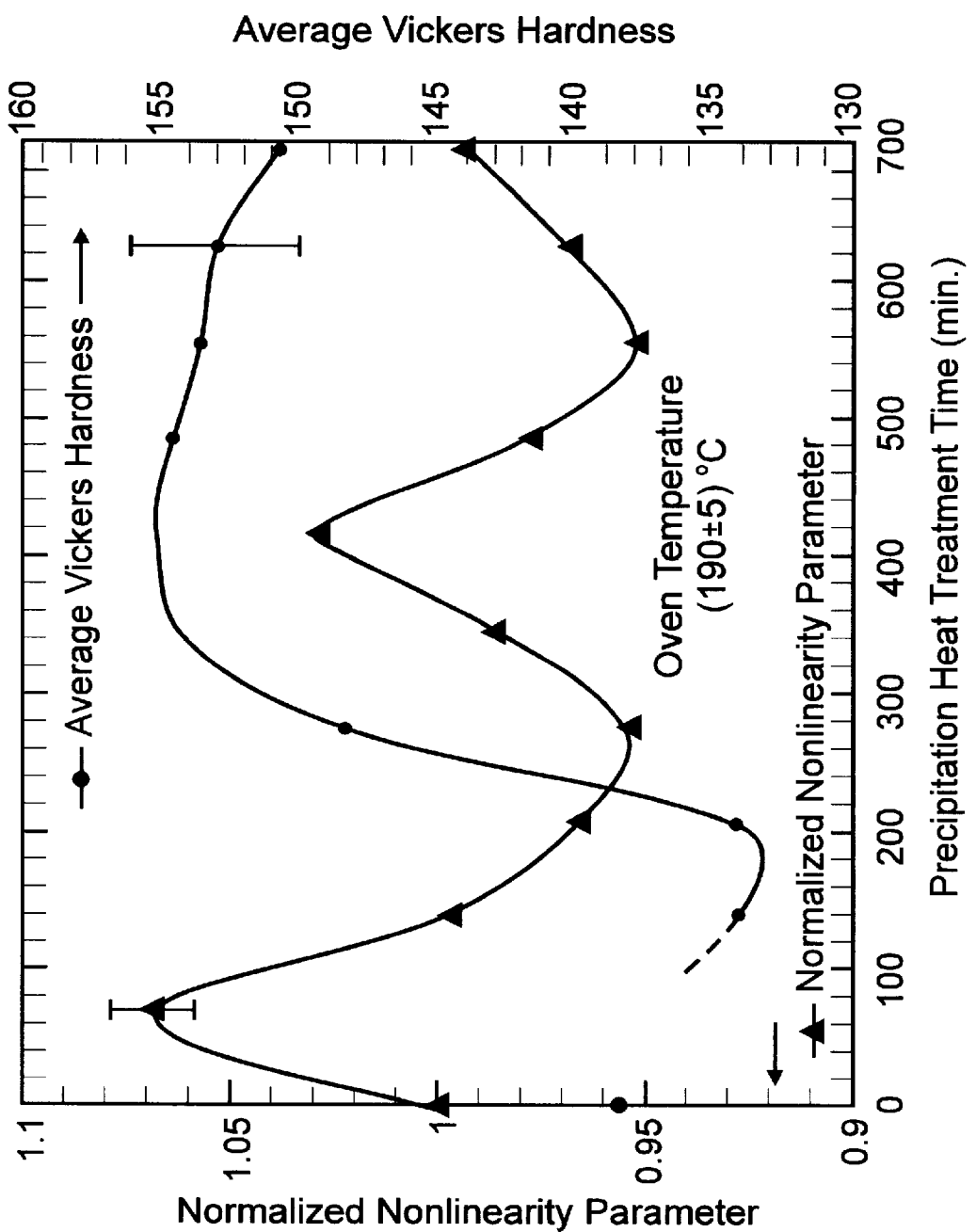
FIG. 1 shows a graph of a series of measurements of average Vickers hardness against precipitation heat treatment time for 2024 Aluminum alloy. It also shows a series of calculated values for the normalized acoustic nonlinearity parameter against precipitation heat treatment time.

The results of the measurements are given in FIG. 1 which show graphs of the acoustic nonlinearity parameter and the measured Vickers hardness, both plotted as a function of heat treatment time (step 6). The nonlinearity parameter is normalized with respect to the value for the T4 temper.

It can be seen that two distinct peaks appear on the graph of nonlinearity parameter. The first peak can be explained in terms of the precipitation and reversion of GP zones. When heat treatment begins, the samples are warmed from approx. 25° C. to a temperature of 190° C. As the temperature rises in the samples, GP zones begin to precipitate more rapidly than had been occurring in the samples while stored at room temperature due to natural aging. The more rapid precipitation of GP zones produces an increase in the strength and in the value of the nonlinearity parameter as the result of the coherency strains generated. This process continues until the GP zone solvus temperature of approximately 180° C. is reached. At this point a dissolving of the GP zones back into the matrix occurs, resulting in decreases in the coherency strains and thus in the material strength and in the value of the nonlinearity parameter.

At the dissolution of the GP zones, the growth of S' precipitates begins. The S' precipitates are the primary strengthening precipitates of the material. A second peak in the nonlinearity parameter curve appears, corresponding to the growth of these precipitates. The second peak corresponds to a maximum Vickers hardness measured for the material. Beyond this time, over aging begins to occur and the nonlinearity parameter drops as does the hardness of the material.

Figure 3:
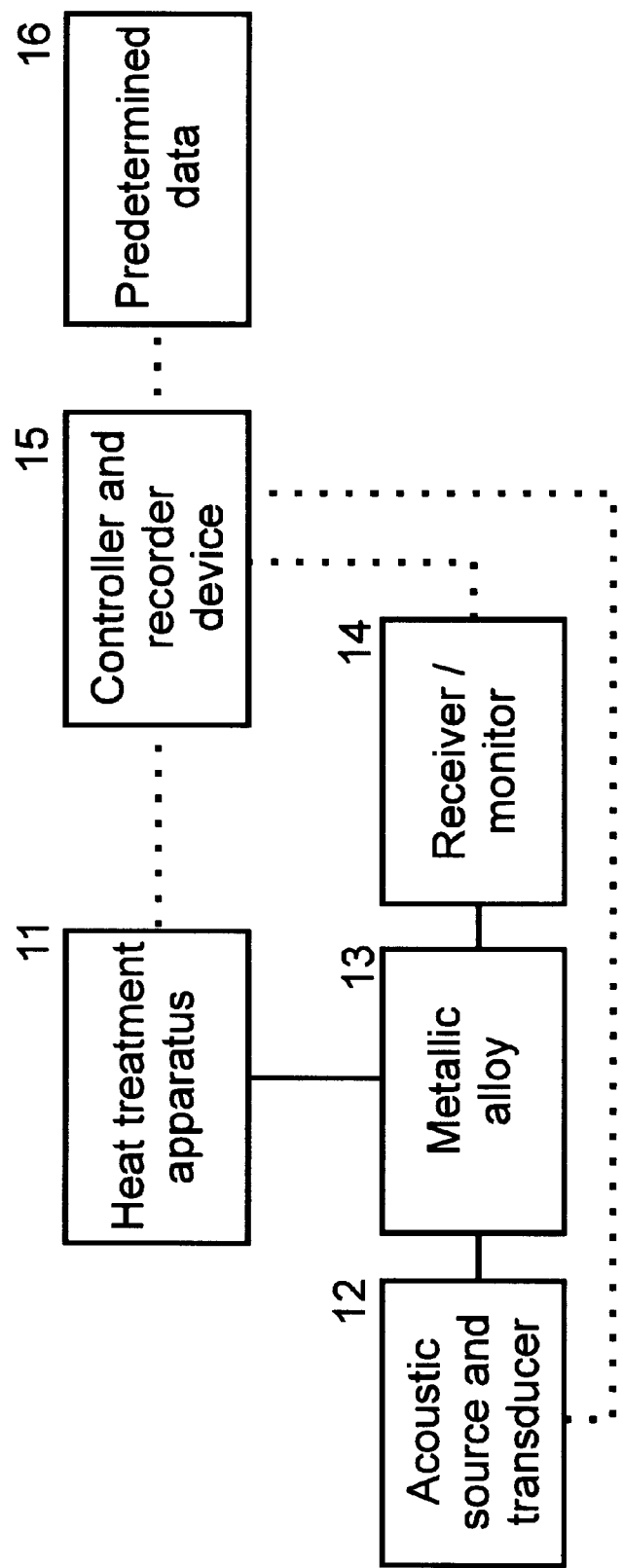
FIG. 3 schematically illustrates one possible embodiment of the present invention.

FIG. 3 is a schematic representation of one possible embodiment of the present invention. In this embodiment, a workpiece 13, made from a heat treatable metallic alloy is prepared for heat treatment by heat treatment apparatus 11. An acoustic source and transducer 12 is acoustically coupled to the workpiece. As the workpiece 13 is heat treated, it is simultaneously insonified by the acoustic source and transducer 12. The resulting signal is monitored by the receiver/monitor 14. For example, in at least one embodiment, in a known manner, the receiver/monitor 14 can include a transducer, a filter for isolating and measuring the fundamental signal, and a filter for isolating and measuring the second harmonic signal of the resultant signal. A controller and recorder device 15 (which in at least one embodiment can be in the form of a computer) can be operatively connected to the heat treatment apparatus 11, the acoustic source and transducer 12 and the receiver/monitor 14. In at least one embodiment, the controller and recorder device 15 can be supplied predetermined data 16, which predetermined data 16 can include, for example, one or more expected measurements of at least a portion of the monitored resulting signal, such as the second harmonic.

In one possible embodiment, the controller and recorder device 15 can utilize the signal measurements provided by the receiver/monitor 14 to calculate the acoustic nonlinearity parameter, which nonlinearity parameter, as described hereinabove, can be used to indicate the changes in material strength or hardness (see FIG. 1). In another possible embodiment of the present invention, the heat treatment apparatus 11 can heat treat the metallic alloy 13 prior to the insonification by the acoustic source and transducer 12.

Other variations will be readily apparent to those of skill in the art. The forgoing is not intended to be an exhaustive list of modifications but rather is given by way of example. It is understood that it is in no way limited to the above embodiments, but is capable of numerous modifications within the scope of the following claims.

We claim:

1. A method for determining optimum heat treatment time for a precipitation hardened material during processing comprising the steps of:

providing a first specimen of a heat treatable metallic alloy;

heat treating the first specimen;

insonifying the first specimen during the heat treatment, and monitoring changes in a resulting signal over time;

providing data derived from the heat treating of a second specimen of the heat treatable metallic alloy, wherein the shape of the first specimen and the shape of the second specimen need not correspond to one another;

the data comprising a desired measurement of at least a portion of the monitored resulting signal, wherein the desired measurement of at least a portion of the monitored resulting signal substantially corresponds to a desired metallic alloy characteristic measurement; and utilizing the data to permit the ceasing of the heat treatment upon monitoring the desired measurement.

2. The method for determining optimum heat treatment time for a precipitation hardened material during processing according to claim 1, wherein said step of monitoring changes in a resulting signal comprises monitoring a fundamental signal and a second harmonic signal of the resulting signal.

3. The method for determining optimum heat treatment time for a precipitation hardened material during processing according to claim 2, wherein said step of providing data comprising a desired measurement of at least a portion of the monitored resulting signal comprises providing data comprising a desired measurement of the second harmonic signal.

4. The method for determining optimum heat treatment time for a precipitation hardened material during processing according to claim 3, wherein the desired metallic alloy characteristic is one of: strength and hardness.

5. The method for determining optimum heat treatment time for a precipitation hardened material during processing according to claim 4, wherein:
   said step of monitoring changes in a resulting signal over time comprises using characteristics of the fundamental signal and the second harmonic signal of the resulting signal to calculate an acoustic nonlinearity parameter; and
   said step of providing data comprising a desired measurement of at least a portion of the monitored resulting signal comprises:
      providing data comprising a desired nonlinearity parameter.

6. The method for determining optimum heat treatment time for a precipitation hardened material during processing according to claim 4, wherein said step of monitoring a fundamental signal and a second harmonic signal of the resulting signal, further comprises:
   monitoring the amplitude of the fundamental signal; and
   keeping the fundamental signal at a constant amplitude.

7. The method for determining optimum heat treatment time for a precipitation hardened material during processing according to claim 6, wherein:
   said step of providing data comprising a desired measurement of the second harmonic signal comprises determining the desired measurement of the second harmonic signal;
   said step of determining the desired measurement comprises:
      providing a sample of the heat treatable metallic alloy;
      heat treating the sample;
      insonifying at least a portion of the sample at designated time intervals during the heat treatment, and measuring at the time intervals a fundamental signal and a second harmonic signal of the resulting signal;
   measuring the metallic alloy characteristic of the at least a portion of the sample at each of the time intervals; and
   determining which measurement of the second harmonic signal corresponds to the desired metallic alloy characteristic measurement.

8. The method for determining optimum heat treatment time for a precipitation hardened material during processing according to claim 5, wherein said step of providing data comprising a desired nonlinearity parameter comprises determining the desired nonlinearity parameter;
   said step of determining the desired nonlinearity parameter comprises:
      providing a sample of the heat treatable metallic alloy;
      heat treating the sample;
      insonifying at least a portion of the sample at designated time intervals during the heat treatment, and monitoring at the time intervals a fundamental signal and a second harmonic signal of the resulting signal;
   using characteristics of the fundamental signal and the second harmonic signal to calculate an acoustic nonlinearity parameter at each of the time intervals;
   measuring the metallic alloy characteristic of the at least a portion of the sample at each of the time intervals; and
   determining which nonlinearity parameter calculation corresponds to the desired metallic alloy characteristic measurement.

9. The method for determining optimum heat treatment time for a precipitation hardened material during processing according to claim 7, wherein:
   the desired measurement of the second harmonic signal comprises a peak in the second harmonic signal corresponding to one of: a maximum hardness and strength; and
   said step of ceasing the heat treatment upon monitoring the desired measurement comprises ceasing the heat treatment upon monitoring the desired peak.

10. The method for determining optimum heat treatment time for a precipitation hardened material during processing according to claim 8, wherein:
    the desired nonlinearity parameter comprises a peak in the calculated nonlinearity parameters corresponding to one of: a maximum hardness and a maximum strength; and
    said step of ceasing the heat treatment upon determining the desired nonlinearity parameter comprises ceasing the heat treatment upon determining the peak.

11. The method for determining optimum heat treatment time for a precipitation hardened material during processing according to claim 9, wherein the data comprises at least one of: expected changes in the second harmonic signal over time during heat treatment, and expected changes in one of: metallic alloy strength and hardness, over time during heat treatment.

12. The method for determining optimum heat treatment time for a precipitation hardened material during processing according to claim 10, wherein the data comprises at least one of: expected changes in the nonlinearity parameter over time during heat treatment, and expected changes in one of: metallic alloy strength and metallic alloy hardness, over time during heat treatment.

13. A method for determining optimum heat treatment time for a precipitation hardened material comprising the steps of:
    providing a first specimen of a heat treatable metallic alloy;
    heat treating the first specimen;
    insonifying the first specimen, and monitoring a resulting signal;
    providing data derived from the heat treating of a second specimen of the heat treatable metallic alloy, wherein the shape of the first specimen and the shape of the second specimen need not correspond to one another;
    the data comprising expected changes in a least a portion of the resulting signal over time during heat treatment, wherein the expected changes substantially correspond to changes in a metallic alloy characteristic; and
    comparing the monitored resultant signal to the data to permit the determination of the substantially corresponding metallic alloy characteristic measurement.

14. The method for determining optimum heat treatment time for a precipitation hardened material according to claim 13, including the step of adjusting the length of the heat treatment, if necessary, such that a desired measurement of the at least a portion of the resulting signal is achieved.

15. The method for determining optimum heat treatment time for a precipitation hardened material according to claim 14, wherein said step of monitoring a resulting signal comprises monitoring a fundamental signal and a second harmonic signal of the resulting signal.

16. The method for determining optimum heat treatment time for a precipitation hardened material according to claim 15, wherein said step of adjusting the length of the heat treatment, if necessary, such that a desired measurement of the at least a portion of the resulting signal is achieved comprises adjusting the length of the heat treatment, if necessary such that a desired measurement of the second harmonic signal is achieved.

17. The method for determining optimum heat treatment time for a precipitation hardened material according to claim 16, wherein said step of monitoring a fundamental signal and a second harmonic signal of the resulting signal, further comprises:

monitoring the amplitude of the fundamental signal; and keeping the fundamental signal at a constant amplitude.

18. The method for determining optimum heat treatment time for a precipitation hardened material according to claim 16 wherein:

said step of monitoring a resulting signal comprises using characteristics of the fundamental signal and the second harmonic signal to calculate an acoustic nonlinearity parameter; and said step of providing data comprising expected changes in a least a portion of the resulting signal over time during heat treatment comprises providing data comprising expected changes in the acoustic nonlinearity parameter.

19. The method for determining optimum heat treatment time for a precipitation hardened material according to claim 17, wherein said step of providing data comprising expected changes in a least a portion of the resulting signal over time during heat treatment comprises providing data comprising expected changes in the second harmonic signal.

20. The method for determining optimum heat treatment time for a precipitation hardened material according to claim 19, wherein:

said step of providing data comprising expected changes in the second harmonic signal comprises determining the expected changes;

said step of determining the expect changes comprises:

providing a sample of the heat treatable metallic alloy;

heat treating the sample;

insonifying at least a portion of the sample at designated time intervals during the heat treatment, and monitoring at the time intervals a fundamental signal and a second harmonic signal of the resulting signal; and measuring the metallic alloy characteristic of the at least a portion of the sample at each of the time intervals.

21. The method for determining optimum heat treatment time for a precipitation hardened material according to claim 18, wherein said step of providing data comprising expected changes in the acoustic nonlinearity parameter comprises determining the expected changes in the nonlinearity parameter;

said step of determining the expected changes in the nonlinearity parameter comprises:

providing a sample of the heat treatable metallic alloy;

heat treating the sample;

insonifying at least a portion of the sample at designated time intervals during the heat treatment, and monitoring at the time intervals a fundamental signal and a second harmonic signal of the resulting signal; and using characteristics of the fundamental signal and the second harmonic signal of the resulting signal to calculate an acoustic nonlinearity parameter at each of the time intervals; and measuring a metallic alloy characteristic at each of the time intervals.

22. The method for determining optimum heat treatment time for a precipitation hardened material according to claim 21, wherein the measured metallic alloy characteristic is one of: strength and the hardness.

23. The method for determining optimum heat treatment time for a precipitation hardened material according to claim 20, wherein the measured metallic alloy characteristic is one of: strength and the hardness.

24. The method for determining optimum heat treatment time for a precipitation hardened material according to claim 23, wherein the data indicates expected changes in the metallic alloy characteristic over time during heat treatment.

25. The method for determining optimum heat treatment time for a precipitation hardened material according to claim 22, wherein the data indicates expected changes in the metallic alloy characteristic over time during heat treatment.

26. The method for determining optimum heat treatment time for a precipitation hardened material according to claim 24, wherein:

the desired measurement of the second harmonic signal comprises a peak in the expected changes in the second harmonic signal, wherein the peak corresponds to one of: a maximum hardness and a maximum strength.

27. The method for determining optimum heat treatment time for a precipitation hardened material according to claim 25, wherein:

the desired nonlinearity parameter comprises a peak in the data indicating an expected change in the nonlinearity parameter corresponding to one of a maximum hardness and a maximum strength.

28. A device for determining optimum heat treatment time for a precipitation-hardened material comprising:

apparatus to heat treat a first specimen of a heat treatable metallic alloy;

an arrangement to insonify the the first specimen, and to monitor a resulting signal;

data derived from the heat treating of a second specimen of the heat treatable metallic alloy, wherein the shape of the first specimen and the shape of the second specimen need not correspond to one another;

the data comprising a desired measurement of at least a portion of the monitored resulting signal, wherein the desired measurement substantially corresponds to a desired metallic alloy characteristic; and means for comparing the resultant signal to the data, the comparing means being operatively connected to the insonifying and monitoring arrangement, to permit the determination of whether or not the desired metallic alloy characteristic has at least substantially been achieved.

29. The device for determining optimum heat treatment time for a precipitation-hardened material according to claim 28, wherein:

the arrangement to insonify the metallic alloy metallic alloy, and to monitor a resulting signal comprises apparatus to measure a fundamental signal and a second harmon signal of the resulting signal;

the data indicates a desired measurement of the second harmonic signal; and the means for comparing the monitored signal to the data comprises means for comparing the monitored second harmonic signal to the data.

30. The device for determining optimum heat treatment time for a precipitation-hardened material according to claim 29 comprising means for adjusting the length of the heat treatment, if necessary, such that the desired measurement of the second harmonic signal is achieved.

31. The device for determining optimum heat treatment time for a precipitation-hardened material according to claim 30 wherein the apparatus to measure a fundamental signal and a second harmonic signal of the resulting signal, further comprises:

monitoring the amplitude of the fundamental signal; and keeping the fundamental signal at a constant amplitude.

32. The device for determining optimum heat treatment time for a precipitation-hardened material according to claim 30 wherein:

the data indicates a desired nonlinearity parameter;

the means for comparing the monitored signal to the data comprises:

means for utilizing characteristics of the fundamental signal and the second harmonic signal to calculate an acoustic nonlinearity parameter, and means for comparing the calculated acoustic nonlinearity parameter with the data.

33. The device for determining optimum heat treatment time for a precipitation-hardened material according to claim 31, further comprising:

means for determining the data, comprising:

apparatus to heat treat a sample of the heat treatable metallic alloy;

an arrangement to insonify at least a portion of the sample at designated time intervals during the heat treatment, means for monitoring at the designated time intervals a resulting signal; and means for measuring at the designated time intervals a characteristic of the at least a portion of the sample.

34. The device for determining optimum heat treatment time for a precipitation-hardened material according to claim 32 further comprising:

means for determining the data, comprising:

apparatus to heat treat a sample of the heat treatable metallic alloy;

an arrangement to insonify at least a portion of the sample at designated time intervals during the heat treatment, means for monitoring at the designated time intervals a fundamental signal and a second harmonic signal of a resulting signal; and means for utilizing characteristics of the fundamental signal and the second harmonic signal to calculate an acoustic nonlinearity parameter at each of the time intervals; and means for measuring at the designated time intervals a characteristic of the at least a portion of the sample.

35. The device for determining optimum heat treatment time for a precipitation-hardened material according to claim 33, wherein the measured metallic alloy characteristic is one of: strength and the hardness.

36. The device for determining optimum heat treatment time for a precipitation-hardened material according to claim 34, wherein the measured metallic alloy characteristic is one of: strength and the hardness.

37. The device for determining optimum heat treatment time for a precipitation-hardened material according to claim 35, wherein the data indicates expected changes in the second harmonic signal over time during heat treatment.

38. The device for determining optimum heat treatment time for a precipitation-hardened material according to claim 36, wherein the data indicates expected changes in the nonlinearity parameter over time during heat treatment.

39. The device for determining optimum heat treatment time for a precipitation-hardened material according to claim 37, wherein:

the desired measurement of the second harmonic signal comprises a peak in the expected changes in the second harmonic signal, wherein said peak corresponds to one of: a maximum hardness and a maximum strength.

40. The device for determining optimum heat treatment time for a precipitation-hardened material according to claim 38, wherein:

the desired nonlinearity parameter comprises a peak in the data indicating an expected change in the nonlinearity parameter corresponding to one of: a maximum hardness and a maximum strength.

41. The device for determining optimum heat treatment time for a precipitation-hardened material according to claim 39, wherein the data comprises expected changes in one of metallic alloy strength and hardness, over time during heat treatment.

42. The device for determining optimum heat treatment time for a precipitation-hardened material according to claim 40, wherein the data comprises expected changes in one of: metallic alloy strength and metallic alloy hardness, over time during heat treatment.

43. A device for determining optimum heat treatment time for a precipitation-hardened material comprising:

apparatus to heat treat a first specimen of a heat treatable metallic alloy;

an arrangement to insonify the the first specimen, and to monitor a resulting signal;

data derived from the heat treating of a second specimen of the heat treatable metallic alloy, wherein the shape of the first specimen and the shape of the second specimen need not correspond to one another;

the data comprising expected changes in at least a portion of the monitored resulting signal, wherein the expected changes substantially correspond to expected changes in a metallic alloy characteristic; and means for comparing the resultant signal to the data, the comparing means being operatively connected to the insonifying and monitoring arrangement, to permit the determination of whether or not a desired metallic alloy characteristic measurement has at least substantially been achieved.

44. The device for determining optimum heat treatment time for a precipitation-hardened material according to claim 33, further comprising:

means for determining the data, comprising:

apparatus to heat treat a sample of the heat treatable metallic alloy;

an arrangement to insonify at least a portion of the sample at designated time intervals during the heat treatment, means for monitoring at the designated time intervals a resulting signal; and means for measuring at the designated time intervals a characteristic of the at least a portion of the sample.

* * * * *